United States Patent [19]

Takeuchi et al.

[11] Patent Number: 4,469,882

[45] Date of Patent: Sep. 4, 1984

[54] PROCESS FOR THE PRODUCTION OF AROMATIC CARBAMATES

[75] Inventors: Tsutomu Takeuchi; Mineo Nishi; Toshio Irie; Hirotaka Ryuto, all of Fukuoka, Japan

[73] Assignee: Mitsubishi Chemical Industries Limited, Tokyo, Japan

[21] Appl. No.: 395,068

[22] PCT Filed: Oct. 22, 1981

[86] PCT No.: PCT/JP81/00293

§ 371 Date: Jun. 23, 1982

§ 102(e) Date: Jun. 23, 1982

[87] PCT Pub. No.: WO82/01550

PCT Pub. Date: May 13, 1982

[30] Foreign Application Priority Data

Oct. 23, 1980 [JP] Japan .............................. 55-148828

[51] Int. Cl.$^3$ ............... C07C 125/065; C07C 125/073
[52] U.S. Cl. ........................................ 560/25; 560/9; 560/14; 560/24; 560/29; 560/30; 549/470

[58] Field of Search ................... 560/25, 9, 14, 24, 29, 560/30; 549/470

[56] References Cited

U.S. PATENT DOCUMENTS 4,262,130  4/1981  Becker et al. ..................... 560/25 X Primary Examiner—Bernard Helfin
Attorney, Agent, or Firm—Sughrue, Mion, Zinn, Macpeak and Seas

[57] ABSTRACT

A process for producing aromatic carbamates in high yield is described, which comprises reacting aromatic nitro compounds, organic compounds containing a hydroxy group, and carbon monoxide in the presence of a catalyst comprising: (1) a platinum group metal or its compound, (2) metallic vanadium or its compound, (3) metallic iron or its compound, (4) a halogen atom, and (5) a tertiary amine, wherein the amount of each component used and the composition are adjusted within specific ranges.

14 Claims, No Drawings

PROCESS FOR THE PRODUCTION OF AROMATIC CARBAMATES

FIELD OF THE INVENTION

The present invention relates to a process for the production of aromatic carbamates. More particularly, it is concerned with a process for the production of aromatic carbamates which comprises reacting an aromatic nitro compound, an organic compounds containing a hydroxy group and carbon monoxide in the presence of a catalyst.

BACKGROUND OF THE INVENTION

Aromatic isocyanates are used as starting materials for the preparation of polyurethane and, commercially, they are usually prepared by reacting aromatic amines obtained by hydrogen-reduction of aromatic nitro compounds with phosgene. This method, however, is rather complicated and, furthermore, has disadvantages in that it utilizes phosgene which is a toxic gas, and hydrogen chloride is generated at the phosgenation reaction, causing the problem of corrosion of equipment.

In recent years, therefore, several methods of production of aromatic isocyanates not using phosgene have been proposed. For example, there is known a method in which aromatic nitro compounds are reacted with compounds containing a hydroxy group and carbon monoxide in a liquid phase in the presence of a catalyst to prepare the corresponding aromatic carbamates and, thereafter, the carbamates are thermally decomposed to obtain aromatic isocyanates. This method requires a catalyst exhibiting high catalytic activity in a small amount in the preparation of aromatic carbamates. Conventional catalysts which have heretofore been proposed include a catalyst comprising (1) a platinum group metal, e.g., palladium, (2) a Lewis acid, e.g., ferrous chloride, and (3) a tertiary amine, e.g., pyridine (see Japanese Patent Application (OPI) No. 98240/76(the term "OPI" is used herein to mean a "published unexamined Japanese patent application")), and a catalyst comprising (1) palladium, (2) vanadium oxychloride, and (3) a tertiary amine (see Japanese Patent Application (OPI) No. 22339/79). Although these catalysts have fairly high catalytic activity, there has been proposed a further improved catalyst comprising (1) a platinum group metal, (2) a Lewis acid, e.g., ferrous chloride, and (3) an oxide or an acid salt of a metal, e.g., vanadium (see Japanese Patent Application (OPI) No. 128550/79).

These conventional catalysts, however, are not considered to have sufficient catalytic activity for practical use and, furthermore, since considerably large amounts of iron and/or vanadium compounds are used, they suffer from disadvantages in that the amount of the metal or metals being incorporated into the desired product crystals is increased when the crystals are separated by crystallization after the completion of the reaction.

As a result of extensive investigations to overcome the above-described problems and to provide a catalyst which exhibits a high catalytic activity even in a small amount, it has been found that a catalyst comprising a platinum group metal, vanadium, iron, a halogen atom, and a tertiary amine wherein the amounts of vanadium and iron used are reduced and the amount of the halogen atom to the total atom of the metals is controlled within a specific range prevents corrosion of equipment, inhibits the formation of by-products, particularly those which cannot be converted into the desired product, and produces the desired aromatic carbamate in high yield.

DISCLOSURE OF THE INVENTION

The present invention, therefore, relates to a process for producing an aromatic carbamate by reacting an aromatic nitro compound, an organic compound containing a hydroxy group and carbon monoxide in the presence of a catalyst, which is characterized in that the catalyst comprises (1) from 0.5 to 20 mmol of a platinum group metal or its compound (in this case, calculated as the metal), (2) from 1 to 70 mmol of metallic vanadium or its compound (in this case, calculated as the vanadium metal), (3) from 0.3 to 50 mmol of metallic iron or its compound (in this case, calculated as the iron metal), (4) from 30 to 400 mmol of a halogen atom, and (5) a tertiary amine, all being based on one kilogram of the organic compound containing a hydroxy group to be fed to the reaction system, and the molar ratio of the halogen atom to all the metals being from 0.5/1 to 60/1.

The invention will hereinafter be explained in detail.

Aromatic nitro compounds which can be used in the invention include mononitrobenzenes, such as nitrobenzene, nitrotoluene, nitroxylene, chloronitrobenzene, bromonitrobenzene, nitrophenyl carbamate, nitroanisol, nitrobenzaldehyde, nitrobenzoyl chloride, ethyl-p-nitrobenzoate, nitrobenzenesulfonyl chloride, and nitrophthalic anhydride; dinitrobenzenes, such as dinitrobenzene, 2,4- or 2,6-dinitrotoluene, 1-chloro-2,4-dinitrobenzene, and 1-fluoro-2,4-dinitrobenzene; and trinitrobenzenes, such as 2,4,6-trinitrotoluene. In addition, nitronaphthalenes, nitrobiphenyls, bis(nitrophenyl)alkanes, bis(nitrophenyl)ethers, bis(nitrophenyl)thioethers, bis(nitrophenyl)sulfonic acids, bis(nitrophenoxy)alkanes, heteroaromatic nitro compounds, etc., can be used. These compounds can be used alone or in combination with each other.

Organic compounds containing a hydroxy group which can be used in the invention include monohydric alcohols, such as methanol, ethanol, propanol, butanol, amyl alcohol, hexanol, lauryl alcohol, cetyl alcohol, cyclohexyl alcohol, benzyl alcohol, and chlorobenzyl alcohol; polyhydric alcohols, such as ethylene glycol, diethylene glycol, propylene glycol, glycerine, and hexanetriol; monohydric phenols, such as phenol, propylphenol, butylphenol, β-naphthol, anthrol, and phenanthrol; and polyhydric phenols, such as catechol, resorcine, pyrogallol, and dihydroxydiphenylmethane. These alcohols or phenols may be substituted by a substituent or substituents which are inert to the reaction, such as a halogen atom, a sulfonic acid group, and a carboxylate group. The above-described compounds can be used alone or in combination with each other.

In the reaction between the aromatic nitro compound and the organic compound containing a hydroxy group, it is theoretically required to use these compounds in such amounts that the molar ratio of the hydroxy group of the organic compound containing a hydroxy group to the nitro group of the organic nitro compound is 1/1. In the invention, however, it is usually preferred that a solvent is not used, but that the organic compound containing a hydroxy group is added in such an amount that the molar ratio of the hydroxy group to the nitro group exceeds 1/1, so that the organic compound containing a hydroxy group also acts as a solvent. For example, the organic compound containing a hydroxy group is used in such an amount that the molar ratio of the hydroxy group to the nitro group is from 2/1 to 400/1 and preferably from 5/1 to 50/1.

The catalyst of the invention essentially comprises (1) a platinum group metal or its compound, (2) metallic vanadium or its compound, (3) metallic iron or its compound, (4) a halogen atom, and (5) a tertiary amine.

Examples of the above catalyst component (1) (i.e., platinum group metal component) include palladium, rhodium, ruthenium, platinum, iridium, and osmium, and their compounds, such as halides, e.g., chlorides and bromides; cyanides; thiocyanides; oxides; inorganic acid salts, e.g., sulfates, nitrates and carbonates; and organic acid salts, e.g., oxalates and acetates. Of these metals and their compounds, palladium and its compounds, particularly halides and oxides are preferred. More preferred are metallic palladium, palladium chloride, and palladium oxide. The platinum group metal component may be deposited on a support, such as activated carbon, graphite, and diatomaceous earth, in an amount of from 0.2 to 5% by weight. The amount of the platinum group metal component (being used) is from 0.5 to 20 mmol, preferably from 0.8 to 15 mmol, as calculated as a metal per one kilogram of the organic compound containing a hydroxy group to be fed to the reaction system. When the amount of the platinum group metal component added is too small, no sufficient catalytic activity can be obtained.

Examples of the catalyst component (2) (i.e., vanadium component) include vanadium and its compounds, such as halides, e.g., vanadium trichloride, vanadium tetrachloride, vanadium oxydichloride, vanadium oxytrichloride, vanadium pentachloride, vanadium tribromide, vanadium tetrabromide, vanadium oxytribromide, vanadium triiodide, vanadium pentaiodide, vanadium oxydiiodide, and vanadium oxytriiodide; oxides, e.g., vanadium trioxide and vanadium pentoxide; vanadic acids and their salts, e.g., pyrovanadic acid, metavanadic acid, sodium orthovanadate, potassium metavanadate, and ammonium metavanadate; sulfates, e.g., vanadium sulfate and vanadyl sulfate; oxalates, e.g., vanadium oxalate and vanadyl oxalate; carbonates, e.g., vanadium carbonate and vanadyl carbonate; vanadium acetylacetonate; vanadium oxyacetylacetonate; VO(OC$_2$H$_5$)$_3$; and V(CO)$_6$. Of these compounds, the halides, oxides, oxalates, and carbonates of vanadium, vanadium acetylacetonate, and VO(OC$_2$H$_5$)$_3$ are preferred. The amount of the vanadium component used is from 1 to 70 mmol, preferably from 2 to 60 mmol, as calculated as a metal per one kilogram of the hydroxy-containing organic compound. When the amount of the vanadium component is outside the above-specified range, no satisfactory results can be obtained. The vanadium component is added in such an amount that the molar ratio of the metal in the vanadium component to the metal in the platinum group metal component is from 0.1 to 15 and preferably from 0.5 to 12.

As the catalyst component (3) (i.e., iron component), metallic iron and iron compounds, such as iron halides, e.g., ferrous chloride, ferric chloride, ferrous bromide, ferric bromide, and ferrous iodide; iron oxides, e.g., ferrous oxide and ferric oxide; iron hydroxides; iron sulfates, e.g., ferrous sulfate and ferric sulfate; iron carbonates, e.g., ferrous carbonate and ferric carbonate; iron oxalates, e.g., ferrous oxalate and ferric oxalate; iron acetylacetonate, and iron phthalocyanine can be used. Of these compounds, metallic iron, and the halides, oxides, hydroxides, carbonates and oxalates of iron are preferred. The amount of the iron component (used) is from 0.3 to 50 mmol, preferably from 0.5 to 30 mmol, as calculated as a metal per one kilogram of the hydroxy group-containing organic compound. Usually the molar ratio of the metallic iron in the iron component to the metal in the platinum group metal component is within the range of from 0.02/1 to 12/1 and preferably from 0.1/1 to 10/1. When the amount of the iron component is outside the above-specified range, sufficiently high catalytic activity cannot be obtained. The molar ratio of the metallic iron in the iron component to the metal in the vanadium component is usually from 0.01/1 to 20/1 and preferably from 0.05/1 to 10/1. As in the case of the platinum group metal component, the vanadium component and the iron component may be deposited on a support. In this case, the components may be deposited on the same support or different supports.

The halogen atom of the catalyst component (4) is used in the form of hydrogen halide, such as hydrogen chloride, hydrogen bromide, or hydrogen iodide. A preferred halogen atom is chlorine, which is preferably used as hydrogen chloride. Although the hydrogen halide can be supplied directly to the reaction system, it is preferred to supply as a tertiary amine-hydrogen halide salt as described hereinafter. In addition, the halogen atom can be used in the form of halides of platinum group metal, vanadium or iron as described hereinbefore. These metal halides may be used in combination with the above tertiary amine-hydrogen halide salt. The amount of the halogen atom used is from 30 to 400 mmol, preferably from 40 to 300 mmol, per one kilogram of the organic compound containing a hydroxy group, and the molar ratio of the halogen atom to all the metals is 0.5/1 to 60/1 and preferably from 0.8/1 to 40/1. When the amount of the halogen atom used is too small, no sufficient catalytic acitvity can be obtained, whereas when it is to large, undesirable side-reactions occur.

Tertiary amines which can be used as the catalyst component (5) of the present invention include aliphatic amines, e.g., triethylamine, tripropylamine, and tributylamine; aromatic amines, e.g., N,N-dimethylaniline, N,N-diethylaniline, and triphenylamine; alicyclic amines, e.g., N,N-dimethylcyclohexylamine, N,N-diethylcyclohexylamine, and N,N-dipropylcyclohexylamine; heterocyclic amines such as pyridine, pyridine derivatives, e.g., chloropyridine, bromopyridine, fluoropyridine, 2,6-dichloropyridine, 4-phenylpyridine, picoline, 2-methyl-5-ethylpyridine, 2,6-lutidine, collidine, 2-vinylpyridine, 2-chloro-4-methylpyridine, 4-phenylthiopyridine, 2-methoxypyridine, 2,6-dicyanopyridine, phenyl α-picolinate, methyl α-picolinate, and α-picolinic acidamide, quinoline, quinoline derivatives, e.g., isoquinoline, chloroquinoline, and 5,6,7,8-tetrahydroquinone, pyrrole derivatives, imidazole derivatives, indole derivatives, and carbazole derivatives. Of these compounds, pyridine, quinoline, isoquinoline, and their derivatives are preferred. The amount of the tertiary amine (used) is from 10 to 5,000 mmol, preferably from 100 to 3,000 mmol, per one kilogram of the hydroxy group-containing organic compound. Usually the molar ratio of the tertiary amine to the halogen atom is from 0.01/1 to 20/1, preferably from 1/1 to 10/1. When the amount of the tertiary amine (used) is too large, the rate of reaction is reduced, whereas when it is to small, the corrosion of reaction equipment is undesirably accelerated. Where a hydrogen halide salt is used as a tertiary amine, it acts as both the tertiary amine component and the hydrogen halide component.

The reaction of the invention can be carried out either batchwise or continuously. In the batchwise method, an aromatic nitro compound, an organic compound containing a hydroxy group, and a catalyst are charged into a reaction system, temperature of the reaction system is raised and, thereafter, the pressure in the reaction system is increased by introducing thereinto carbon monoxide and the reaction is carried out under stirring. The reaction temperature is usually from 100° to 250° C., preferably from 140° to 200° C., and the reaction pressure is usually from 1 to 200 kg/cm$^2$, preferably from 30 to 100 kg/cm$^2$. The reaction time is usually from 10 minutes to 15 hours, preferably from 1 to 10 hours.

After the reaction is completed, the reaction mixture is passed through a filter to separate the platinum group metal component, etc., which are present in a solid form and, thereafter, the mother liquor is cooled to precipitate aromatic carbamate crystals which are then recovered by filtration. Since the mother liquid usually contains the catalyst components other than the platinum group metal component, it is preferably recycled to the reaction system and reused.

The catalyst of the invention exhibits greatly high catalytic activity even when it is used in a small amount. In particular, the amounts of the vanadium component and the iron component used are small and, therefore, when the deisred product is crystallized out after the completion of the reaction, the amount of metals contained in the crystals formed is reduced and furthermore the loss of the catalyst is decreased.

Best Mode of the Invention

The following examples are given to illustrate the invention in greater detail although the invention is not limited thereto. The concentrations of the catalyst components mean the amounts of each metal in the metallic component of the catalyst, halogen atom, and tertiary amine per one kilogram of the organic compound containing a hydroxy group.

EXAMPLE 1

A 1.5-liter autoclave made of titanium was charged with 38.25 g of 2,4-dinitrotoluene (hereinafter referred to as "DNT") and 300 ml of ethanol which had been dehydrated by the use of molecular sieves and, furthermore, with 5.0 g of metallic palladium deposited on activated carbon in an amount of palladium metal of 2% by weight (Pd concentration: 3.95 mmol/kg), 369 mg of VCl$_3$ (V concentration: 9.9 mmol/kg), 228 g of FeCl$_3$ (Fe concentration: 5.93 mmol/kg), 2.5 g of a pyridine hydrochloric acid salt (Cl concentration: 139 mmol/kg; including Cl in the metallic compound), and 6.09 g of pyridine. After the atmosphere in the autoclave was replaced by N$_2$ gas, the temperature was raised to 140° C. and CO gas was introduced under pressure to 80 kg/cm$^2$G and, thereafter, the temperature was raised to 160° C. The reaction was carried out under stirring for 4 hours.

After the reaction was completed, the autoclave was allowed to cool and to return to the atmospheric pressure. The reaction mixture was filtered, and the filtrate was analyzed by high-speed liquid chromatography to determine the yields of the desired product, diethyltolylene-2,4-dicarbamate (hereinafter referred to as "diurethane"), an intermediate product, ethyl-methylnitro carbanilate (hereinafter referred to as "nitrourethane"), and a by-product, ethyl-methylamino carbanilate (hereinafter referred to as "aminourethane"). The results are shown in Table 1.

COMPARATIVE EXAMPLES 1–4

The procedure of Example 1 was repeated wherein the catalyst component of vanadium or iron compound was not used. The results are shown in Table 1.

TABLE 1

| No. | Composition and Concentration of Catalyst Component | | | Yield | |
|---|---|---|---|---|---|
| | V (mmol/kg) | Fe (mmol/kg) | Cl/All Metals (molar ratio) | Di-urethane (%) | Nitro-urethane (%) |
| Example 1 | 9.90 | 5.93 | 7.01 | 96 | 0 |
| Comparative Example 1 | — | 5.93 | 11.0 | 14 | 76 |
| Comparative Example 2 | — | 15.8 | 7.01 | 23 | 66 |
| Comparative Example 3 | 9.90 | — | 8.73 | 34 | 57 |
| Comparative Example 4 | 15.8 | — | 7.01 | 53 | 40 |

COMPARATIVE EXAMPLES 5–11

The procedure of Example 1 was repeated wherein the concentration of each catalyst component was varied. The concentration of each catalyst component, the ratio of Cl/all metals, and the results are shown in Table 2. The Cl concentration includes the Cl in the metallic compounds.

TABLE 2

| Comparative Example | Composition and Concentration of Catalyst Component | | | | | Yield (%) | | |
|---|---|---|---|---|---|---|---|---|
| | Pd (mmol/kg) | V (mmol/kg) | Fe (mmol/kg) | Cl (mmol/kg) | Cl/All Metals (molar ratio) | Diurethane (%) | Nitro-urethane (%) | Amino-urethane (%) |
| 5 | 0.40 | 9.90 | 5.93 | 139 | 8.6 | 5 | 78 | 0 |
| 6 | 3.95 | 0.50 | 5.93 | 139 | 13.0 | 38 | 53 | 0 |
| 7 | 3.95 | 80.0 | 5.93 | 139 | 1.5 | 80 | 6 | 3 |
| 8 | 3.95 | 9.90 | 0.15 | 139 | 9.9 | 69 | 24 | 1 |
| 9 | 3.95 | 9.90 | 60.0 | 139 | 1.9 | 78 | 8 | 2 |
| 10 | 3.95 | 9.90 | 5.95 | 20 | 1.0 | 3 | 77 | 0 |
| 11 | 3.95 | 9.90 | 5.95 | 500 | 25.0 | 79 | 1 | 8 |

EXAMPLES 2–6

The procedure of Example 1 was repeated under the reaction conditions shown in Table 3 and using the catalyst components shown in Table 4. The results are shown in Table 5.

TABLE 3

| Example No. | DNT (g) | Ethanol (ml) | Reaction Temperature (°C.) | Reaction Pressure (kg/cm² G) | Reaction Time (hr) |
|---|---|---|---|---|---|
| 2 | 78.0 | 300 | 160 | 90 | 4 |
| 3 | 38.25 | 300 | 160 | 80 | 4 |
| 4 | 40.0 | 300 | 170 | 80 | 5 |
| 5 | 38.25 | 300 | 165 | 90 | 4 |
| 6 | 80.0 | 300 | 160 | 80 | 4 |

TABLE 4

| Ex. | Platinum Group Metal Component | | Vanadium (Va) Component | | Iron (Fe) Component | | Halogen Atom | | Halogen Atom/All Atoms (molar ratio) | Tertiary Amine | |
|---|---|---|---|---|---|---|---|---|---|---|---|
| | Compound | Concentration | Compound | Concentration | Compound | Concentration | Compound | Concentration | | Compound | Concentration |
| 2 | 2% Pd/C | 6.33 | VO(acac)₂ | 19.8 | Fe(acac)₂ | 8.9 | iQ.HCl | 250 | 7.13 | iQ | 750 |
| 3 | 2% Pd/C | 2.77 | VO(OC₂H₅)₃ | 11.1 | FeCl₂-Py₂ | 11.1 | Py.HCl | 190 | 7.6 | Py | 308 |
| 4 | RhCl₃ | 5.23 | VOCl₃ | 3.92 | Fe | 0.786 | Q.HCl | 253 | 25.5 | Q | 506 |
| 5 | 2% Pd/C | 3.16 | V₂O₅ | 11.9 | FeCl₃ | 5.93 | Py.HCl | 127 | 6.0 | Py | 127 |
| 6 | 2% Pd/C | 7.91 | VCl₃ | 19.8 | FeCl₃ | 11.9 | Py.HCl | 277 | 7.0 | Py | 831 |

Note 1
Concentration: mmol/kg
Pd/C: Palladium deposited on activated carbon
Py: Pyridine
Q: Quinoline
iQ: Isoquinoline
acac: CH₃COCHCOCH₃
Note 2
The concentration of halogen atom is a value including the halogen contained in the metallic compound. Also the concentration of tertiary amine is a value including the tertiary amine contained in the tertiary amine-hydrogen halide salt, and in the metallic compound.

TABLE 5

| Example No. | Yield (%) | |
|---|---|---|
| | Diurethane | Nitrourethane |
| 2 | 87 | 1 |
| 3 | 91 | 0 |
| 4 | 90 | 0 |
| 5 | 92 | 0 |
| 6 | 93 | 0 |

EXAMPLES 7–8 AND COMPARATIVE EXAMPLES 12–13

The procedure of Example 1 was repeated using the catalyst components shown in Table 6 and the reaction was carried out for 3 hours. The results are shown in Table 7.

TABLE 6

| | Platinum Group Metal Component | | Vanadium (V) Component | | Iron (Fe) Component | | Halogen Atom | | Halogen Atom/All Metals (molar ratio) | Tertiary Amine | |
|---|---|---|---|---|---|---|---|---|---|---|---|
| | Compound | Concentration | Compound | Concentration | Compound | Concentration | Compound | Concentration | | Compound | Concentration |
| Ex. 7 | 2% Pd/C | 3.95 | V₂O₅ | 31.6 | FeCl₂-Py₂ | 15.8 | Py.HCl | 300 | 5.8 | — | 300 |
| Ex. 8 | 2% Pd/C | 0.901 | V₂O₅ | 50 | Fe | 20 | Q.HBr | 300 | 4.23 | — | 300 |
| Comp. Ex. 12 | PdCl₂ | 0.901 | V₂O₅ | 471 | FeCl₂-Py₂ | 242 | — | 486 | 0.68 | — | 484 |
| Comp. Ex. 13 | 2% Pd/C | 4.77 | VOCl₃ | 83.9 | FeCl₃ | 83.9 | — | 503.4 | 2.92 | Py | 257 |

Note
The symbols for the compounds and the concentration of catalyst component are the same as described in Notes 1 and 2 of Table 4.

TABLE 7

| | Yield (%) | | |
|---|---|---|---|
| | Diurethane | Nitrourethane | Aminourethane |
| Example 7 | 92 | 0 | 3 |
| Example 8 | 89 | 2 | 4 |
| Comparative | 79 | 5 | 5 |

TABLE 7-continued

| | Yield (%) | | |
|---|---|---|---|
| | Diurethane | Nitrourethane | Aminourethane |
| Example 12 Comparative Example 13 | 72 | 3 | 7 |

EXAMPLE 9

A feed consisting of 61.50 g of nitrobenzene and 250 ml of ethanol was reacted at 170° C. and 90 kg/cm²G and 5 hours in the presence of a catalyst comprising 2.50 g of activated carbon with 5% of metallic palladium deposited thereon (Pd concentration: 5.93 mmol/kg), 203 mg of VO(COO)₂·H₂O (V concentration: 5.93 mmol/kg), 2.00 g of activated carbon with 4% (as metallic iron) of Fe₂O₃ deposited thereon (Fe concentration: 7.12 mmol/kg), 2.4 g of a pyridine-hydrogen bromide salt and 1.19 g of pyridine (halogen atom concentration: 75.9 mmol/kg; molar ratio of halogen atom to all metals: 4.0/1). The yield of urethane was 94%.

INDUSTRIAL APPLICABILITY

Aromatic carbamates prepared by the method of the invention can be converted into the corresponding aromatic isocyanates. Thus the method of the invention is particularly useful in the production of aromatic isocyanates.

We claim:
1. A process for producing an aromatic carbamate by reacting to a temperature of from 100° to 250° C., at a pressure of from 1 to 100 Kg/cm² and at a time of from 10 minutes to 15 hours an aromatic nitro compound, a monohydric alcohol or a monohydric phenol, and car- bon monoxide in the presence of a catalyst wherein the catalyst comprises:
(1) from 0.5 to 20 mmol of a platinum group metal or a halide, cyanide, thiocyanide, oxide, nitrate, carbonate, sulfate, oxalate or acetate thereof (calculated as a metal);
(2) from 1 to 70 mmol of metallic vanadium or its compound (calculated as vanadium metal);
(3) from 0.3 to 50 mmol of metallic iron or its compound (calculated as iron metal);
(4) from 30 to 40 mmol of a halogen atom; and
(5) from 10 to 5,000 mmol of a heterocyclic amine, all of the above (1) thru (5) being calculated per one kilogram of the monohydric alcohol or monohydric phenol fed to the reaction system, and the molar ratio of halogen atom to all metals is from 0.5/1 to 60/1.

2. The process as claimed in claim 1, wherein the platinum group metal or its compound is metallic palladium or a halide, cyanide, thiocyanide, oxide, nitrate, carbonate, sulfate, oxalate or acetate thereof.

3. The process as claimed in claim 2, wherein the palladium compound is a halide, oxide, nitrate, carbonate sulfate, oxalate or acetate of palladium.

4. The process as claimed in claim 1, wherein the vanadium compound is a halide, oxide, oxalate or carbonate of vanadium, vanadium acetylacetonate, or VO(OC$_2$H$_5$)$_3$.

5. The process as claimed in claim 1, wherein the iron compound is a halide, oxide, hydroxide, sulfate, carbonate or oxalate of iron, iron acetylacetonate, or iron phthalocyanine.

6. The process as claimed in claim 1, wherein the halogen atom is chlorine or bromine.

7. The process as claimed in claim 6, wherein the halogen atom is used as hydrogen halide.

8. The process as claimed in claim 1, wherein the heterocyclic amine is pyridine, quinoline, isoquinoline or a derivative thereof.

9. The process as claimed in any of claims 1 to 7 and 8, wherein the aromatic nitro compound is a mononitrobenzene or a dinitrobenzene.

10. The process as claimed in claim 9, wherein the mononitrobenzene is nitrobenzene or nitrotoluene, and the dinitrobenzene is dinitrobenzene or dinitrotoluene.

11. The process as claimed in claim 1, wherein the monohydric alcohol is methanol or ethanol, and the monohydric phenol is phenol.

12. The process as claimed in claim 1, wherein the molar ratio of the hydroxy group in the monohydric alcohol or monohydric phenol to the nitro group in the aromatic nitro compound is from 2/1 to 400/1.

13. The process as claimed in claim 1 wherein the catalyst comprises:
(1) from 0.8 to 15 mmol of the platinum group metal or halide, cyanide, thiocyanide, oxide, nitrate, carbonate, sulfate, oxalate or acetate thereof (calculated as a metal);
(2) from 2 to 60 mmol of metallic vanadium or its compound (calculated as vanadium metal);
(3) from 0.5 to 30 mmol of metallic iron or its compound (calculated as iron metal);
(4) from 40 to 300 mmol of the halogen atom; and
(5) from 100 to 3,000 mmol of the tertiary heterocyclic amine, all of the above (1) thru (5) being calculated per one kilogram of the monohydric alcohol or monohydric phenol, and the molar ratio of halogen atom to all metals being from 0.8/1 to 40/1.

14. The process as claimed in claim 1, wherein the molar ratios of the catalyst components are as follows:
(i) vanadium/platinum group metal=0.1/1 to 15/1;
(ii) iron/platinum group metal=0.02/1 to 12/1;
(iii) iron/vanadium=0.01/1 to 20/1; and
(iv) tertiary heterocyclic amine/halogen atom=0.01/1 to 20/1.

* * * * *